(12) United States Patent
Sernfält

(10) Patent No.: US 12,239,580 B2
(45) Date of Patent: Mar. 4, 2025

(54) EYE-PROTECTION HEADGEAR

(71) Applicant: 3M INNOVATIVE PROPERTIES COMPANY, St. Paul, MN (US)

(72) Inventor: Mats U. Sernfält, Leksand (SE)

(73) Assignee: 3M Innovative Properties Company, St. Paul, MN (US)

( * ) Notice: Subject to any disclaimer, the term of this patent is extended or adjusted under 35 U.S.C. 154(b) by 788 days.

(21) Appl. No.: 16/867,790

(22) Filed: May 6, 2020

(65) Prior Publication Data

US 2020/0261274 A1    Aug. 20, 2020

Related U.S. Application Data

(63) Continuation of application No. 14/483,530, filed on Sep. 11, 2014, now abandoned.

(51) Int. Cl.
| | |
|---|---|
| *A61F 9/06* | (2006.01) |
| *A42B 3/22* | (2006.01) |
| *F16P 1/06* | (2006.01) |
| *A61F 9/02* | (2006.01) |

(52) U.S. Cl.
CPC ............. *A61F 9/061* (2013.01); *A42B 3/225* (2013.01); *A61F 9/023* (2013.01); *F16P 1/06* (2013.01)

(58) Field of Classification Search
CPC .......... A61F 9/061; A61F 9/062; A61F 9/064; A61F 9/04; A61F 9/045
USPC ...... 2/172, 173, 184.5, 202, 203, 207, 175.6
See application file for complete search history.

(56) References Cited

U.S. PATENT DOCUMENTS

| | | | |
|---|---|---|---|
| 766,426 A * | 8/1904 | Comstock | A42B 1/046 2/4 |
| 1,205,308 A | 11/1916 | Work | |
| 1,222,995 A * | 4/1917 | Rhoades | A42B 1/046 2/10 |
| 1,856,879 A | 5/1932 | Lufkin | |
| 1,994,103 A | 3/1935 | Huey | |
| 2,212,014 A | 8/1940 | Doyle | |
| 2,249,239 A | 7/1941 | Goldsmith | |
| 2,390,352 A | 12/1945 | Bouchard | |
| 2,436,724 A | 2/1948 | Mishel | |
| 2,457,554 A | 12/1948 | Harding | |
| 2,579,942 A | 12/1951 | Maclean | |
| 2,759,187 A | 8/1956 | Woodard | |
| 2,882,894 A | 4/1959 | Fahey | |
| 2,896,617 A | 7/1959 | Gibbons | |
| 3,026,525 A | 3/1962 | Gyorfy | |
| 3,050,736 A | 8/1962 | Malcom, Jr. | |
| 3,098,233 A | 7/1963 | Hoagland | |
| 3,137,295 A | 6/1964 | Stansfield | |
| 3,427,660 A | 2/1969 | Raschke | |
| 3,868,727 A * | 3/1975 | Paschall | A61F 9/064 2/12 |
| 4,513,452 A | 4/1985 | Rankin, Sr. | |
| 4,556,991 A | 12/1985 | Margaronis | |
| 4,980,928 A | 1/1991 | Ellis | |
| 5,105,475 A | 4/1992 | Lynd | |
| 5,749,096 A | 5/1998 | Fergason | |

(Continued)

FOREIGN PATENT DOCUMENTS

EP          1061822 B1  *  4/2003  ............... A42B 3/10

*Primary Examiner* — Katharine G Kane
(74) *Attorney, Agent, or Firm* — Kenneth B. Wood

(57) ABSTRACT

An eye-protection headgear including a rigid visor with a window bearing an optical filter, and with a flexible fabric bib and a flexible fabric cap.

19 Claims, 4 Drawing Sheets

(56) References Cited

U.S. PATENT DOCUMENTS

| | | | |
|---|---|---|---|
| 5,857,215 | A | 1/1999 | Fergason |
| 6,711,748 | B2 | 3/2004 | Paris |
| 7,093,302 | B1 | 8/2006 | Burns |
| 7,197,774 | B2 | 4/2007 | Curran |
| 7,540,039 | B2 | 6/2009 | Reaux |
| 8,104,094 | B2 | 1/2012 | Uttrachi |
| 8,225,428 | B2 | 7/2012 | Grilliot |
| 2005/0197452 | A1 | 9/2005 | Bersted |
| 2006/0107431 | A1 | 5/2006 | Curran |
| 2007/0245467 | A1* | 10/2007 | Lilenthal ................ A42B 3/225 2/416 |
| 2009/0031485 | A1* | 2/2009 | Prusinski ................ A42B 3/24 2/9 |
| 2009/0055987 | A1 | 3/2009 | Becker |
| 2009/0210988 | A1 | 8/2009 | Becker |
| 2009/0210989 | A1 | 8/2009 | Becker |
| 2010/0263671 | A1 | 10/2010 | Walker |
| 2011/0030114 | A1 | 2/2011 | Merikoski |
| 2011/0185480 | A1 | 8/2011 | Braendle |
| 2011/0219506 | A1 | 9/2011 | Uttrachi |
| 2014/0190486 | A1 | 7/2014 | Dunn |
| 2014/0215673 | A1 | 8/2014 | Lilenthal |
| 2014/0298557 | A1 | 10/2014 | Townsend, Jr. |
| 2016/0074230 | A1 | 3/2016 | Sernfält |
| 2020/0297060 | A1* | 9/2020 | Berggren ................ A42B 3/225 |

\* cited by examiner

EYE-PROTECTION HEADGEAR

BACKGROUND

Optical filters, such as e.g. automatic darkening filters, are often provided on protective headgear (e.g., welding helmets or the like) where protection from e.g. high intensity light is desired.

SUMMARY

In broad summary, herein is disclosed an eye-protection headgear comprising a rigid visor with a window comprising an optical filter; and, a flexible fabric bib and a flexible fabric cap. The rigid visor is pivotably connected to a head suspension and is pivotably movable relative to the head suspension, between at least a first, shielding position and a second, non-shielding position. These and other aspects will be apparent from the detailed description below. In no event, however, should this broad summary be construed to limit the claimable subject matter, whether such subject matter is presented in claims in the application as initially filed or in claims that are amended or otherwise presented in prosecution.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated.

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match.

Terms such as upward, downward, upper, uppermost, lower, lowermost, above, below, and so on, are defined with respect to a conventional vertical axis that is present when the eye-protection headgear is fitted on the head of a user who is standing upright. (That is, upward means toward the top of FIGS. 1-6; downward means toward the bottom of FIGS. 1-6).

Figure 1:
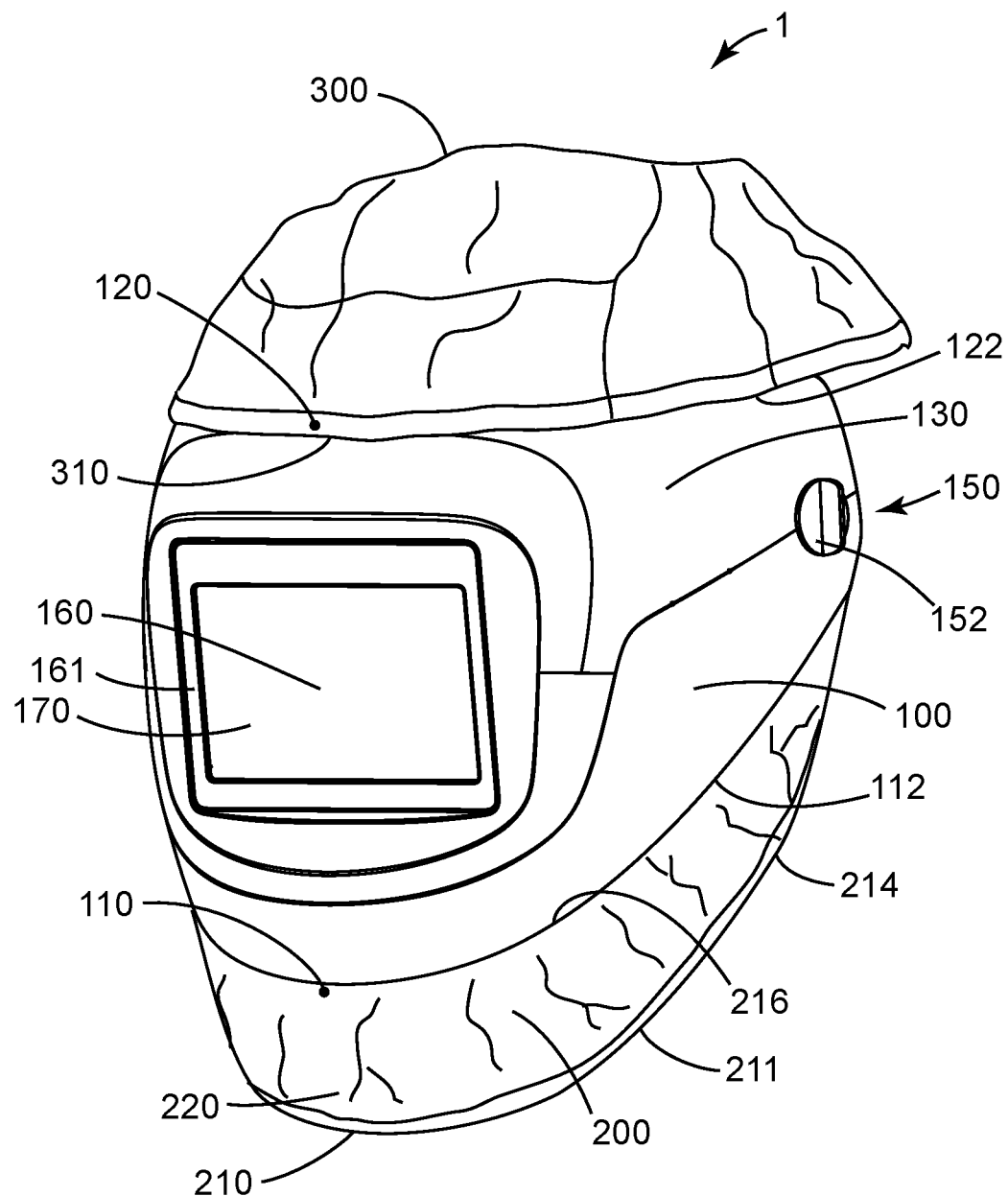
FIG. 1 is a front-side perspective view of an exemplary eye-protection headgear.

Terms such as front, forward, forwardmost, etc., refer to a direction that, when the headgear is fitted on the head of a user, is toward a source of light from which the user's eyes are desired to be shielded. Thus, for example, FIG. 1 is a view from the front side of a headgear. Terms such as rear, rearward, rearwardmost, etc., refer to a direction that is generally away from the front direction. Thus, as viewed in FIG. 5, forward is toward the left side of the Figure; rearward is toward the right side of the Figure. The term "lateral" denotes directions generally orthogonal to the front-rear axis and generally orthogonal to the vertical axis, of the headgear as fitted on the head of a user. Thus, in FIG. 5, the lateral axis runs in and out of plane of the Figure as viewed.

DETAILED DESCRIPTION

Figure 2:
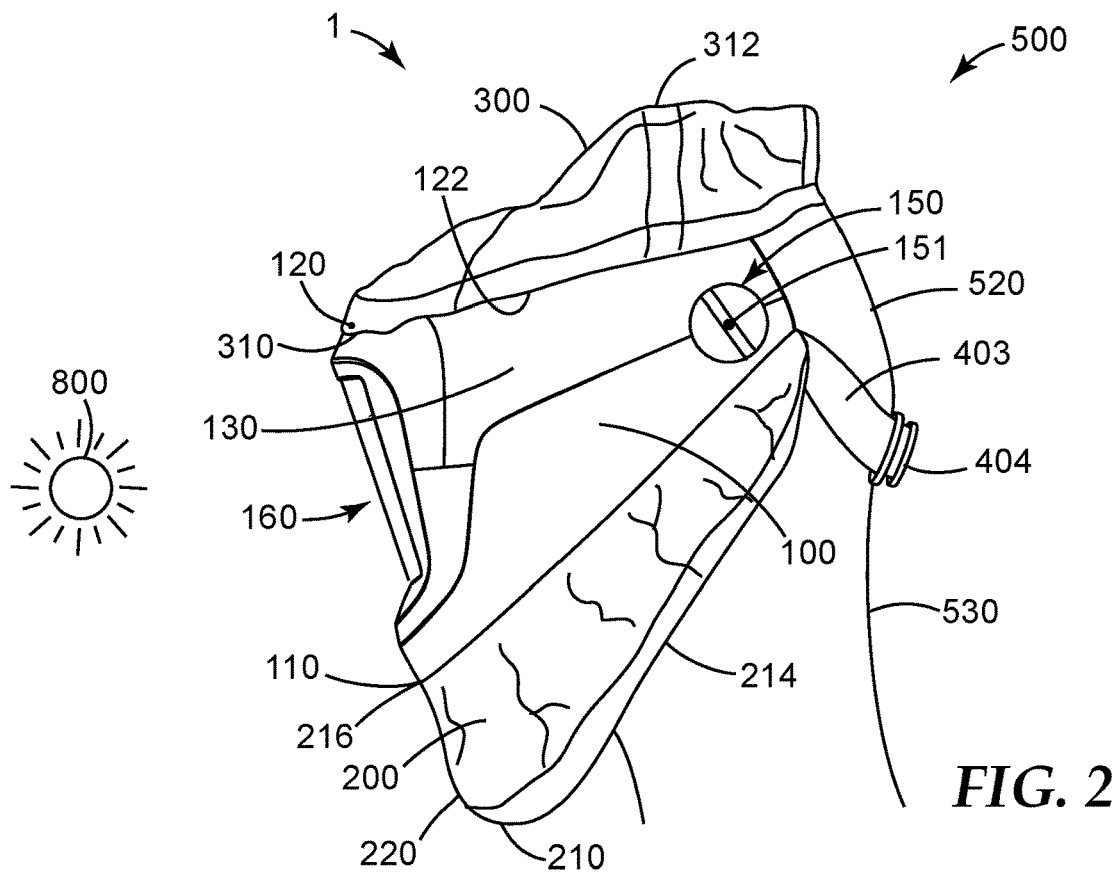
FIG. 2 is a side perspective view of an exemplary eye-protection headgear, in a first, shielding position.
Figure 3:
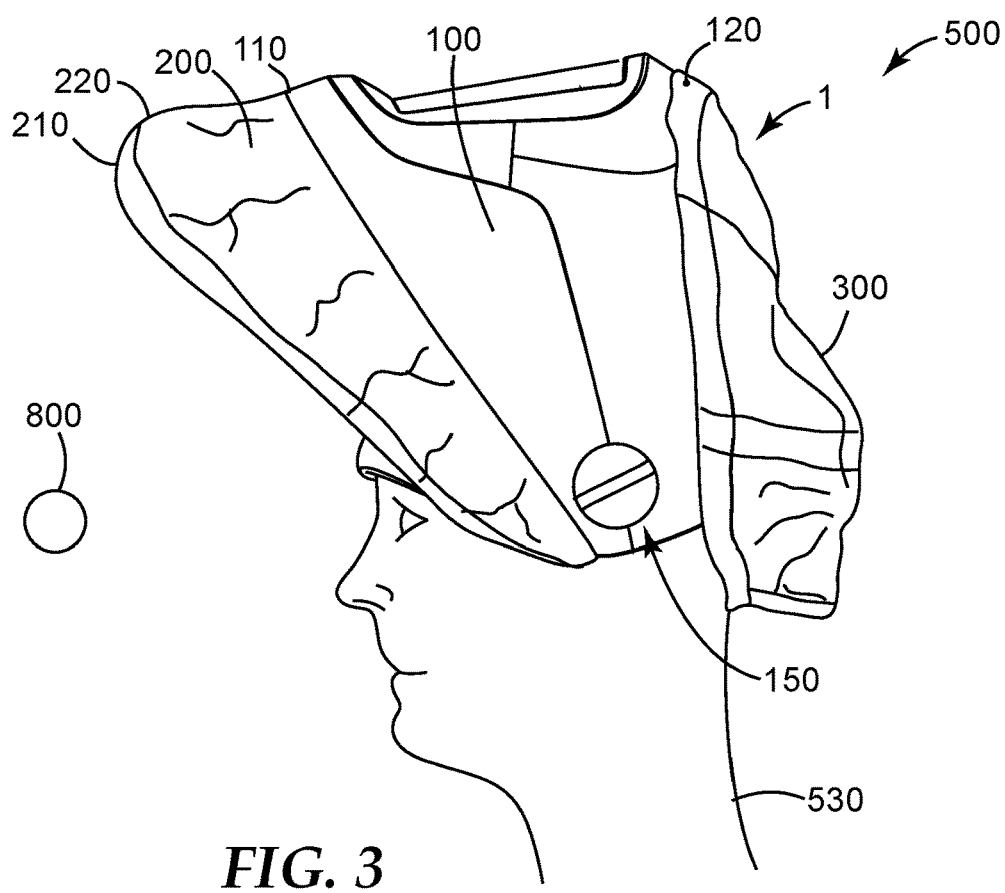
FIG. 3 is a side perspective view of an exemplary eye-protection headgear, in a second, non-shielding position.

Herein is disclosed an eye-protection headgear 1 comprising an opaque rigid visor 100 comprising a window 160 comprising an optical filter 170, as depicted in exemplary embodiment in FIG. 1. Headgear 1 further comprises a flexible fabric bib 200 extending at least generally downward from a lower edge 110 of at least a forward portion of visor 100. Headgear 1 further comprises a flexible fabric cap 300 extending at least generally rearward from an upper edge 120 of at least a forward portion of visor 100. Visor 100 is pivotably connected to a head suspension 400 (not visible in the view FIG. 1, but visible in exemplary embodiment e.g. in FIGS. 4 and 5) and is pivotably movable relative to head suspension 400, between at least a first, shielding position and a second, non-shielding position. Shielding positions are defined with headgear 1 fitted on the head of a user with the user in an upright position (e.g. as shown in FIGS. 2 and 3); by a shielding position is meant a position in which light from a light source 800 (e.g. a welding workpiece) in front of the user's face can reach the user's eyes only by way of passing through window 160 of visor 100. An exemplary shielding position is depicted in FIG. 2. By a non-shielding position is meant a position in which light from a light source in front of the user can reach the user's eyes without having to pass through window 160 (e.g. such light is able to reach the eyes by passing underneath a lower edge 210 of bib 200). An exemplary non-shielding position is depicted in FIG. 3.

In at least some embodiments, when the visor is in a second, non-shielding position, lower edge 210 of at least a forward portion 220 of fabric bib 200 is above the level of the eyes of the user of the headgear (as shown in FIG. 3). The pivotable connection between visor 100 and head suspension 400 can be configured so that visor 100 can be pivotably moved to a position that is sufficiently far upward that this may be achieved. In various embodiments, visor 100 is pivotably movable relative to the head suspension, through an angle of at least about 70, 80, 90, 100, or 110 degrees. (FIGS. 2 and 3 in combination depict an exemplary embodiment in which pivotable movement through an angle of at least about 90-100 degrees is allowed).

Visor 100 may be configured to enhance the ability to move visor 100 into a non-shielding position (i.e., to put headgear 1 into a non-shielding configuration). Thus, in some embodiments, a forwardmost point of lower edge 110, and a forwardmost point of upper edge 120, of visor 100 may combine to exhibit an included angle that is relatively small. Such an included angle may be conveniently measured from a vertex that coincides with an axis of rotation of the pivotable connection between the visor and the head suspension (such an axis of rotation is signified by reference number 151 in FIG. 2, and in FIG. 2 runs in and out of plane). In various embodiments, a forwardmost point of lower edge 110 and a forwardmost point of upper edge 120 may combine to exhibit an included angle of no more than about 70, 60, or 50 degrees. In further embodiments, such portions may combine to exhibit an included angle of at least about 30, 40, or 50 degrees. (FIG. 2 depicts an exemplary embodiment in which such an included angle appears to be in the range of about 50-55 degrees).

In this context it is noted that terms such as forward, as used herein to describe portions of visor 100, are used to distinguish generally forwardly-located portions of visor 100 from generally laterally-located (side) portions of visor 100. Thus, a forward portion of visor 100 is not limited to being a single most forwardly located point of visor 100 (e.g., of edge 110 of visor 100); rather, it may signify an area that extends e.g. several cm in lateral width. The skilled person will appreciate that the forward portion of visor 100 (and e.g. forward portions of items such as edges 110 and 120) will often straddle the sagittal plane of the user's head and may extend e.g. symmetrically for a few centimeters (e.g., 1-2 cm) to each lateral side of the sagittal plane. In contrast, terms such as a forwardmost point as used for the specific purpose of characterizing an included angle, will specifically denote the most forwardly-located point of edge 110 and of edge 120. Similar considerations apply to the use of terms such as forward portions and forwardmost points, in describing components such as bib 200 and cap 300 and edges thereof.

Visor 100 is a rigid visor, to which is attached a flexible fabric bib 200. The terms rigid and flexible are used herein to distinguish the bending stiffness of visor 100 relative to bib 200; by rigid is meant that visor 100 exhibits a bending stiffness that is at least about 50 times the bending stiffness of bib 200. (In further embodiments, visor 100 may exhibit a bending stiffness that is at least about 100, 200, or 500 times that of bib 200.) However, by rigid is not meant that visor 100 must necessarily be extremely stiff in the manner of e.g. a metal plate or the like. Thus, although visor 100 may be made from any suitable material, in some embodiments rigid visor 100 may be conveniently molded from any suitable thermoplastic or thermoset polymeric molding material, with the inherent properties of the material and the thickness of the visor (e.g., from about 0.5 mm to about 2 mm) being chosen in combination to provide the rigidity appropriate for an eye-protection visor, as will be well understood by the ordinary artisan. Visor 100 may thus be molded of e.g. any suitable resin such as, but not limited to, polyolefins, nylons, polycarbonates, and so on. Such a resin may be chosen to have appropriate temperature resistance, may be filled with any desired reinforcing filler (e.g. one or more of mineral fillers, glass fibers, carbon fibers, and so on), as desired.

Visor 100 is opaque, meaning that it passes essentially no (e.g., less than 0.0001%) light therethrough. In some embodiments visor 100 may pass less than 0.00001, or 0.000001, % of light therethrough. Such arrangements may be achieved e.g. by including one or more opacifying fillers in the resin used to make visor 100. Such fillers may be chosen from e.g. mineral fillers (e.g., pigments) such as talc, calcium carbonate, titanium dioxide, barium sulfate, and so on, and/or from fillers such as carbon black. Any suitable dye or dyes may be present as well, as desired.

As noted, visor 100 comprises a lower edge and an upper edge. In FIG. 1, reference numbers 110 and 120 indicate the forward portions of these edges (with the lines from the reference numbers being drawn to the forwardmost points of these edges). Reference numbers 112 and 122 respectively denote lateral portions of the lower and upper edges.

Visor 100 comprises window 160 located in a forward portion thereof. Window 160 is optically transmissive (e.g., so as to transmit at least about 10, 20, 40, or 80% of visible light therethrough). In the simplest embodiment, window 160 can be a through-opening; or, it may comprise e.g. a clear pane that is permanently mounted to visor 100. Window 160 may be peripherally surrounded by, e.g. defined by, a frame portion 161 of visor 100 as in the exemplary design of FIG. 1. (While in many embodiments window 160 may conveniently be generally rectangular in shape, this is not strictly necessary, and window 160 might be e.g. oval, or might at least have somewhat rounded corners.)

An optical filter 170 is provided in window 160 so that when visor 100 is in the first, shielding position, any light from a light source 800 located in front of the user's eyes must pass through optical filter 170 in order to reach the user's eyes. By optical filter is meant a device (which may comprise of one or more layers) that can allow at least some electromagnetic radiation (e.g., visible light) to pass therethrough but that can also block at least some electromagnetic radiation from passing therethrough.

In some embodiments, optical filter 170 may be configured to block high intensity light. In this context, "light" means electromagnetic radiation and includes at least visible light, and infrared and/or ultraviolet radiation, whether or not such radiation is perceptible to the user. In this context, "high intensity" light means light that is present at an intensity (e.g. such as that emitted by a device such as an arc welder) such that it might be capable of damaging the eyes of a user, or of causing perceived discomfort to the user. Thus, optical filter 170 may be configured to reduce high-intensity light as encountered e.g. in welding operations, to an intensity that is acceptable to a user of headgear 1. An eye-protection headgear with such an optical filter thus might find use e.g. in industrial operations, for example welding (e.g. arc welding, torch welding, acetylene welding), cutting (e.g. laser cutting, acetylene cutting), brazing, soldering and the like.

The light-blocking properties of optical filter 170 may be characterized e.g. by a Shade Number as is commonly known in the art. Thus, in various embodiments optical filter 170 may exhibit a Shade Number of at least about 4, 6, 8, 10, or 12 (or, of any suitable value). If desired, several optical filters of different Shade Number can be provided (e.g. as a kit along with headgear 1), and can be exchanged as desired for particular needs.

In specific embodiments, optical filter 170 may be an automatic darkening filter 180 that includes a switchable shutter that is capable of controllably blocking electromagnetic radiation (i.e., can switch between at least a light state (e.g. in which is it relatively highly light-transmissive) and a dark state (e.g. in which it is relatively non-transmissive to light)). Such a switchable shutter may comprise e.g. one or more liquid crystal layers, polarizing filters, electrochromic materials, etc., as are familiar to those of ordinary skill. If desired, other components (e.g. additives within layers of the shutter, and/or separate layers in the light path) may be provided that constantly block (whether by absorption, reflection, scattering, or some other mechanism) radiation of various wavelengths to a desired degree. For example, one or more constantly ultraviolet-blocking layers, constantly infrared-blocking layers, interference filters, and the like, may be present. Such layers might be provided e.g. as coatings or panes that are built into an automatic darkening filter, or might be provided as separate layers (panes) that are insertable into window 160 either alone or along with an automatic darkening filter, or might be provided as layers that are non-removably built into window 160 of visor 100.

Figure 4:
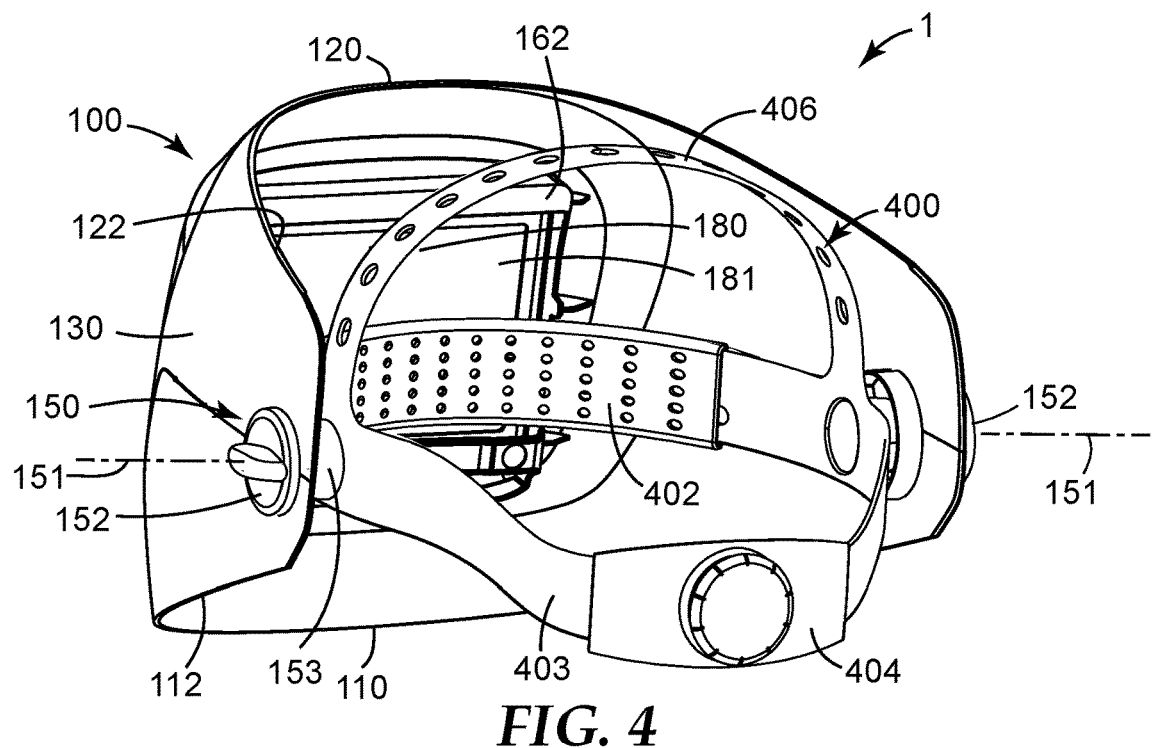
FIG. 4 is a rear-side perspective view of an exemplary rigid visor and an exemplary head suspension.

In some embodiments, an optical filter 170 e.g. comprising an automatic darkening filter 180 may be provided in the form of a cartridge 181 that is removably insertable into window 160 of visor 100, as shown in exemplary embodiment in FIG. 4. Cartridge 181 may be held in place in any suitable manner, e.g. by way of retaining member 162 as depicted in FIG. 4. Such cartridges and manners of removably inserting them into a visor (in general, into a helmet of an eye-protection apparatus) are discussed in further detail in U. S. Patent Application Publication No. 2014/0215673 to Lilenthal, which is incorporated by reference herein.

In some embodiments, an automatic darkening filter 180 may comprise a detector that is capable of detecting e.g. at least the presence of high intensity light, and may further comprise a shutter control system that receives input from the detector and controls the switchable shutter in response. Such an automatic darkening filter may include an internal power supply (e.g., one or more batteries). However, it will be appreciated that any of these components or functionalities (e.g., detector, shutter control system, power supply, detector, and any items or functionalities associated therewith (e.g., wiring, connectors, status indicators, on/off switches and other controls, etc.)) may be located in a separate location (e.g., in a separate module of headgear 1) rather than being located on or within an automatic darkening filter 180 (e.g. a cartridge 181) itself.

Eye-protection headgear 1 includes flexible fabric bib 200, which extends at least generally downward from at least a forward portion of lower edge 210 of rigid visor 100 as shown in exemplary manner in FIGS. 1 and 2. (All uses of terms such as downward, forward, and so on, are specified as being with headgear 1 fitted on the head of a user, and are characterized with respect to a conventional vertical and forward-rearward directions applicable when the eye-protection headgear is fitted on the head of a user who is standing upright, as noted earlier herein.) In the specific exemplary design of FIG. 2, forward portion 220 of bib 200 also extends slightly rearward (toward the neck of the user) in addition to extending generally downward.

Bib 200 is comprised of fabric, by which is meant any fibrous material that is e.g. woven, non-woven, knitted, or the like. Such a fabric may be chosen to have a fiber density, thickness, and so on, commensurate with the needs of e.g. industrial welding (e.g. the fabric may be chosen so to prevent or minimize the ability of sparks, UV or IR radiation, etc., to penetrate therethrough,). Bib 200 is flexible (the term flexible being defined in relation to the rigidity of visor 100 as discussed previously) and is thus compliant and able to be deformed (e.g., at least partially bent, crumpled, folded, crushed, pleated, etc.) e.g. in the act of using headgear 1 in e.g. tight or confined spaces. In particular, bib 200 may be sufficiently flexible to allow the user of headgear 1 to tilt his or her head forward so that even if lower edge 210 of bib 200 contacts the user's chest, bib 200 is able to deform to allow additional tilting of the head. It will be appreciated that, in contrast, the chin-protecting portions of e.g. conventional welding helmets often limit the amount to which the user's head can be tilted forward.

In at least some embodiments, bib 200 may extend at least generally downward not only from a forward portion of lower edge 110 of rigid visor 100, but from side portions 112 of lower edge 110 as well. In particular embodiments, bib 200 may extend at least generally downward from substantially, or essentially, the entire length of lower edge 110 (as in the exemplary embodiment of FIGS. 1 and 2). An upper edge 216 of bib 200 may be attached to visor 100, e.g. at or near lower edge 110 of visor 100. (In this context it is noted that it may not be necessary to specifically attach a terminal upper edge of bib 200 to a terminal lower edge of visor 100; rather, some overlap of bib 200 and visor 100 may be present.) Such attachment may be provided at several locations along the extent of bib 200 and visor 100. For instance, such attachment may be present not only in forward portions of the bib and visor, but also at one or more locations along the side (lateral) portions of these components. Such attachment of bib 200 to visor 100 may be provided by any suitable means, and may be provided at intervals that are spaced along the extent of bib 200 and visor 100 (e.g. by way of studs, rivets, clips, ultrasonic spot-welds, sections of hook-and-loop fasteners, and so on), or may extend at least quasi-continuously along this extent (e.g. by way of adhesive bonding, stitching, continuous ultrasonic welds, continuous hook-and-loop fasteners, and so on). Such attachment may be permanent (meaning that bib 200 cannot be removed from visor 100 without destroying or unacceptably damaging either or both of bib 200 and visor 100); however, in some embodiments bib 200 may be removably attached to visor 100 e.g. so that bib 200 may be removed for cleaning.

Bib 200 may be designed and configured so that it enhances the ability to place headgear 1 into a second, non-shielding configuration merely by pivotably moving visor 100, without necessarily having to manipulate (e.g., fold or remove) bib 200 in order for the user to be able to see in a forward direction. This may be achieved e.g. by configuring the headgear so that when visor 100 is in the second, non-shielding position, forward portion 220 of bib 200 that extends in a generally downward direction when the headgear is in the first, shielding configuration (as shown in FIG. 2), extends in an at least generally forward direction when the headgear is in the second, non-shielding position (as shown in FIG. 3) rather than e.g. drooping or hanging downward. In other words, the headgear may be designed so that when visor 100 is in the second, non-shielding position, bib 200 resists the tendency of gravity to cause forward portion 220 of bib 200 to droop downward into a generally vertical configuration. Thus, in various embodiments, when visor 100 is in the second, non-shielding position, at least forward portion 220 of bib 200 may be oriented at a positive angle of at least about 30, 50, or 70 degrees away from vertical. In the exemplary embodiment of FIG. 3, a forward section of bib 200 appears to be oriented at a positive angle of about 60-70 degrees away from vertical. (In this context, "positive" means in a frontward direction, e.g. clockwise in the view of FIG. 3.)

It will be appreciated that an overall arcuate shape of bib 200 as mounted on visor 100 (as evident in FIG. 1) may facilitate such properties by causing bib 200 to form an at least somewhat self-reinforcing arch when visor 100 is in the second, non-shielding position. Such properties may also be enhanced by appropriate selection of the bending stiffness of bib 200. Such properties may also be enhanced by providing a stiffening beam that runs along at least a portion of lower edge 210 of bib 200 and that forms an at least somewhat self-reinforcing arch when visor 100 is in the second, non-shielding position. Such a stiffening beam may be provided in any suitable manner, e.g. by attaching a flexible member (e.g., a rod or wire) to bib 200, along at least a substantial extent of lower edge 210 of bib 200. In particular embodiments a stiffening beam may be conveniently provided from the fabric of bib 200 itself, by finishing lower edge 210 as a folded hem 211 (e.g., by folding an edge section of bib 200 back on itself to form two layers and sewing the layers together). Such a folded hem may provide a stiffening beam; or, a member (e.g. a rod or wire) may be provided within the hem if desired, to augment the stiffening property of the hem.

Eye-protection headgear 1 includes flexible fabric cap 300, which extends at least generally rearward from at least a forward portion of upper edge 120 of rigid visor 100 as shown in exemplary manner in FIGS. 1 and 2. Cap 300 may be made of any of the fabrics mentioned above with reference to bib 200 and may conveniently be made of the same material as bib 200 although this is not necessarily required.

In addition to extending at least generally rearward from a forward portion of upper edge 120 of visor 100, cap 300 may also extend generally laterally inward from each lateral (side) portion 122 of the upper edge of visor 100, as shown in exemplary embodiment in FIG. 1. A forward edge 310 of cap 300 may be attached to visor 100, e.g. at or near upper edge 120 of visor 100. Lateral edges of cap 300 may likewise be attached to lateral portions of upper edge 120 of visor 100. It may not be necessary to attach a terminal edge of bib 200 to a terminal upper edge of visor 100; rather, some overlap of cap 300 and visor 100 may be present. (In this context it is noted that the term edge as used here and elsewhere herein is synonymous with "edge portion" and thus does not denote solely a terminal edge, but rather encompasses at least a strip of e.g. about 1 cm in width that borders such a terminal edge.) Attachment of cap 300 to visor 100 may be provided at several locations along the extent of cap 300 and visor 100. For instance, such attachment may be present not only in forward locations of the bib and visor, but also at one or more locations along the lateral portions of these components. Such attachment may be provided by any continuous or discontinuous means, and may be permanent or removable, and may include any of the mechanism described above.

In some embodiments, when visor 100 is in the first, shielding position, cap 300 may extend rearward to overlie the crown of the head of the user of headgear 1, as shown in exemplary embodiment in FIG. 2. In further embodiments, when visor 100 is in the first, shielding position, cap 300 may extend downward to reside rearward of the occipital portion of the head of the user, as shown in exemplary embodiment in FIG. 6. In still further embodiments, when visor 100 is in the first, shielding position, cap 300 may extend further downward to reside rearward of the neck of the user, also as shown in exemplary embodiment in FIG. 6. In FIG. 6, crown-protecting, occiput-protecting, and rear neck-protecting portions of cap 300 are respectively indicated by reference numbers 312, 314 and 316. (While the ordinary artisan will be aware of the location of such portions of the human head, for convenience the crown, occiput, and neck of a human head 500 are respectively indicated by reference numbers 510, 520 and 530 in FIG. 5.)

In some embodiments, bib 200 and cap 300 may meet each other on first and second lateral sides of headgear 1 so as to collectively provide lateral neck-protection portions of the headgear. Such an arrangement is shown in exemplary embodiment in FIG. 6 with the approximate meeting point of cap and bib portions being indicated by reference number 340. In such cases, lateral portions of bib 200 and cap 300 may overlap each other (e.g. to a distance of a few cm); or they may be joined to each other. If it is desired to use headgear 1 in combination with a respirator-protective apparatus (that e.g. supplies filtered breathing air to the user), cap 300 may comprise at least one through-opening 350 that is configured to admit an air-delivery hose 351, as shown in FIG. 6.

In embodiments of the type illustrated in FIGS. 1-3, bib 200 may be provided by a first piece of fabric and cap 300 may be provided by a second piece of fabric that is a separate piece from the first piece of fabric and that is not directly connected to the first piece of fabric. Rather, such first and second separate pieces may be separately attached to visor 100. In embodiments of the type illustrated in FIG. 6, bib 200 and cap 300 may be e.g. first and second, integrally-connected portions of a single piece of fabric. Bib 200 and/or cap 300 may be made of flame-retardant fabric if desired.

Eye-protection headgear 1 includes a head suspension. An exemplary head suspension 400 is shown in FIG. 4 although any suitable head suspension may be used. By head suspension is specifically meant an apparatus that bears the weight of visor 100 and supports visor 100 in position upon the head of the user. That is, even though there may be e.g. some incidental contact of fabric cap 300 with the user's head, essentially all of the weight of visor 100 (and thus of optical filter 170) will be born by suspension 400.

As shown in exemplary embodiment in FIG. 4, a head suspension may include e.g. a front headband 402 and a rear headband and/or nape strap 403, and by definition includes one or more top bands 406 that extend at least generally over the user's head (It is not required that any such top band must necessarily extend directly over the topmost point of the user's head, however.) If desired, a rear headband 403 may include an adjustable portion 404 to adjust the fit to the user's head (in the exemplary embodiment of FIG. 4, this portion may be adjusted by way of a rotatable knob). As noted, visor 100 is pivotably connected to suspension 400. This may be provided in any suitable manner, e.g. by way of connecting rearward lateral (side) portions of visor 100 to laterally-extending protrusions 153 of head suspension 400, and holding visor 100 in place by way of caps 152, as shown in FIG. 4. By this or any other suitable of arrangement, the pivotable connecting of visor 100 to suspension 400 may be provided by first and second connections that are located on laterally opposite sides of the user's head, the first and second pivotable connections sharing a common axis of rotation that passes through both the first and second connections (as exemplified by axis of rotation 151 of FIG. 4). It may be convenient to provide that caps 152 can be tightened or loosened to adjust the force required to move visor 100 back and forth between the first and second (shielding and non-shielding) positions.

Figure 5:
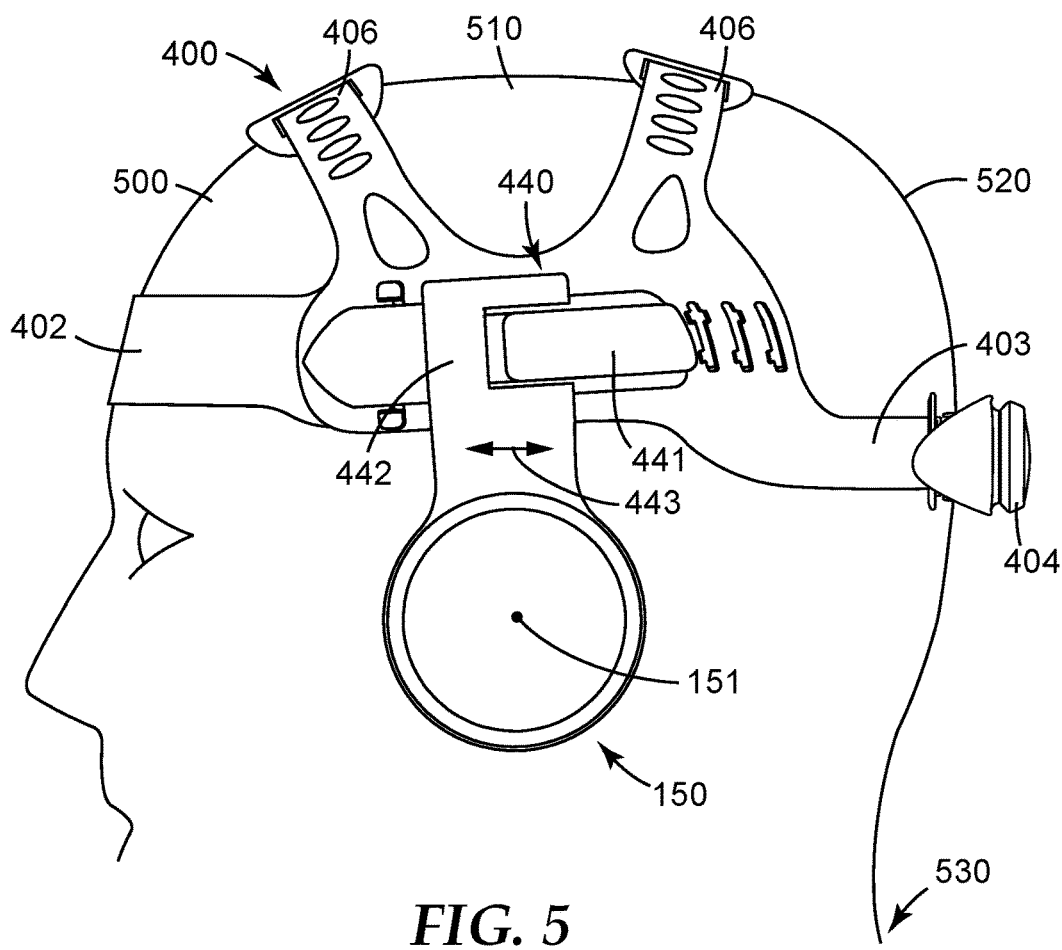
FIG. 5 is a side perspective view of another exemplary head suspension.
Figure 6:
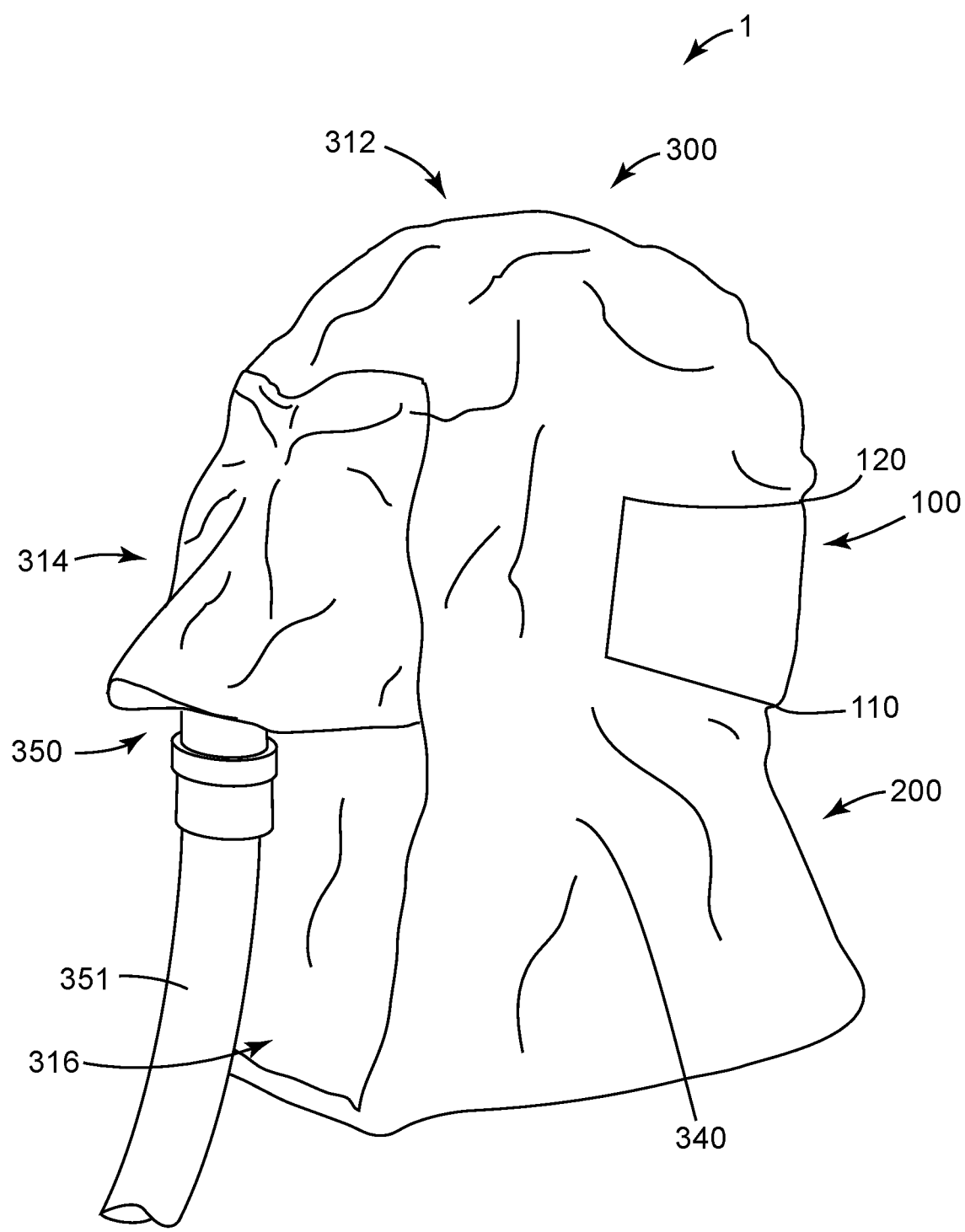
FIG. 6 is a side-rear perspective view of another exemplary eye-protection headgear.

Another exemplary head suspension 400 is depicted in side perspective view in FIG. 5 (with the rigid visor, fabric bib and fabric cap omitted for ease of presentation). FIG. 5 depicts a design in which two top bands 406 are present. Also, the design shown in FIG. 5 allows visor 100 to be slidably movable back and forth in a forward-rearward direction in addition to being pivotably movable between the first and second positions. The ability to slidably move visor 100 allows the distance at which visor 100 is placed from the eyes and nose of the user when visor 100 is in the first, shielding position, to be adjusted as desired. In the particular design shown in FIG. 5, a forward-rearward slidable connection 440 is achieved by providing head suspension 400 with a member 441 that has a long axis oriented at least generally along a forward-rearward axis of the head suspension, and providing a carriage 442 that is slidably movable along beam 441 in a forward-rearward direction (indicated by double-headed arrow 443). Since visor 100 is connected to carriage 442 via pivotable connection 150, moving carriage 442 thus moves visor 100 relative to head suspension 400.

It will be appreciated that the designs and configurations disclosed herein provide an eye-protection headgear in which significant portions (e.g. the bib and cap) of the headgear are compliant (being made of flexible fabric) and can be temporarily deformed, flattened, crushed etc. This can advantageously allow the headgear to be used in the first, shielding position even in a relatively tight or confined space. This is achieved while still providing that the headgear can be placed in a second, non-shielding configuration e.g. merely by pivotably moving the visor. That is, it may not be necessary to e.g. fold or remove the fabric bib in order for the user to be able to see in a forward direction, when the visor is moved to the second, non-shielding position.

The present application is a continuation of application Ser. No. 14/483,530, published as U.S. Patent Application Publication No. 2016/0074230, which is incorporated by reference herein in its entirety.

List of Exemplary Embodiments

Embodiment 1 is an eye-protection headgear comprising: an opaque rigid visor comprising a window comprising an optical filter, a flexible fabric bib extending at least generally downward from a lower edge of at least a forward portion of the rigid visor, and a flexible fabric cap extending at least generally rearward from an upper edge of at least a forward portion of the rigid visor, wherein the rigid visor is pivotably connected to a head suspension and is pivotably movable relative to the head suspension, between at least a first, shielding position and a second, non-shielding position.

Embodiment 2 is the eye-protection headgear of embodiment 1 wherein when the rigid visor is in the second, non-shielding position, a lower edge of at least a forward portion of the flexible fabric bib is above the level of the eyes of a user of the eye-protection headgear. Embodiment 3 is the eye-protection headgear of any of embodiments 1-2 wherein when the rigid visor is in the second, non-shielding position, at least a forward portion of the flexible fabric bib is oriented at a positive angle of at least about 30 degrees away from vertical. Embodiment 4 is the eye-protection headgear of any of embodiments 1-3 wherein at least substantially an entire length of a lower edge of the flexible fabric bib comprises a folded hem that provides a stiffening beam.

Embodiment 5 is the eye-protection headgear of any of embodiments 1-4 wherein a forwardmost point of the lower edge of the rigid visor and a forwardmost point of the upper edge of the rigid visor combine to exhibit an included angle, measured from a vertex that coincides with an axis of rotation of the pivotable connection between the rigid visor and the head suspension, of no more than about 65 degrees. Embodiment 6 is the eye-protection headgear of any of embodiments 1-5 wherein the rigid visor is pivotably connected to the head suspension in such a way that the rigid visor is pivotably movable relative to the head suspension, through an angle of at least about 80 degrees. Embodiment 7 is the eye-protection headgear any of embodiments 1-6 wherein the rigid visor is pivotably connected to the head suspension in such a way that the rigid visor is front-rear slidably movable relative to the head suspension in addition to being pivotably movable relative to the head suspension.

Embodiment 8 is the eye-protection headgear of any of embodiments 1-7 wherein the flexible fabric bib is provided by a first piece of fabric and wherein the flexible fabric cap is provided by a second piece of fabric that is a separate piece from the first piece of fabric and that is not directly connected to the first piece of fabric. Embodiment 9 is the eye-protection headgear of any of embodiments 1-7 wherein the flexible fabric bib and the flexible fabric cap are first and second, integrally-connected portions of a piece of fabric.

Embodiment 10 is the eye-protection headgear of any of embodiments 1-9 wherein when the rigid visor is in the first, shielding position, the flexible fabric cap extends rearward to overlie a crown of a head of a user of the headgear. Embodiment 11 is the eye-protection headgear of any of embodiments 1-10 wherein when the rigid visor is in the first, shielding position, the flexible fabric cap extends downward to reside rearward of an occipital portion of the head of the user of the headgear. Embodiment 12 is the eye-protection headgear of any of embodiments 1-11 wherein when the rigid visor is in the first, shielding position, the flexible fabric cap extends downward to reside rearward of a neck of the user of the headgear.

Embodiment 13 is the eye-protection headgear of any of embodiments 1-12 wherein the flexible fabric bib and the flexible fabric cap portion meet each other on first and second lateral sides of the headgear so as to collectively provide lateral neck-protection portions of the headgear. Embodiment 14 is the eye-protection headgear of any of embodiments 1-13 wherein the flexible fabric cap comprises at least one opening configured to admit an air-delivery hose of a respiratory-protective apparatus. Embodiment 15 is the eye-protection headgear of any of embodiments 1-14 wherein the flexible fabric bib and the flexible fabric cap are each removably attached to the rigid visor. Embodiment 16 is the eye-protection headgear of any of embodiments 1-15 wherein the flexible fabric bib and the flexible fabric cap are each made of flame-retardant fabric.

Embodiment 17 is the eye-protection headgear of any of embodiments 1-16 wherein the optical filter is an automatic darkening filter. Embodiment 18 is the eye-protection headgear of embodiment 17 wherein the automatic darkening filter is in the form of a cartridge that is removably insertable into the window of the rigid visor. Embodiment 19 is the eye-protection headgear of any of embodiments 1-18 wherein the window is peripherally surrounded by, and defined by, a frame portion of the rigid visor, and wherein the rigid visor is made of a molded opaque thermoplastic polymeric material. Embodiment 20 is the eye-protection headgear of any of embodiments 1-19 wherein the pivotable connecting of the rigid visor to the head suspension is provided by first and second connections located on laterally opposite sides of the user's head and wherein an axis of rotation of the pivotable connection passes through both the first and second connections.

Examples

Several prototypes of the general types depicted in FIGS. 1-4 and 6 were made by the following procedures. A conventional welding helmet of the general type available from 3M Company, St. Paul, MN under the trade designation SPEEDGLAS 10V SERIES was obtained. Portions of the helmet were physically removed by cutting to obtain a rigid visor of the approximate size and shape shown in FIG. 4. Sheets of fabric of the general type used in welding protection hood products available from 3M Company under the trade designation (Part No.) 16 91 00 were obtained.

These sheets were cut to a desired size and shape and were attached by various mechanisms (e.g., by stitching or by plastic rivets) to the upper and lower edges of the visor, to form bibs and caps of the general size and shape shown in FIGS. 1-3. In some cases the bib and cap were in the form of separate pieces of fabric that were separately attached to the visor, as in the illustrations of FIGS. 1-3. In other cases an integral design was used in which the bib and cap were integrally connected, as in the illustration of FIG. 6. Numerous headgear prototypes of various designs and configurations were produced. In at least some of the prototypes, when the visor was placed into the aforementioned second, non-shielding position, the lower edge of at least a forward portion of the fabric bib remained above the level of the eyes of a user of the eye-protection headgear (e.g. as depicted in FIG. 3), without it being necessary to manipulate (e.g., fold) the bib in any manner.

The foregoing Examples have been provided for clarity of understanding only, and no unnecessary limitations are to be understood therefrom. The tests and test results described in the Examples are intended to be illustrative rather than predictive, and variations in the testing procedure can be expected to yield different results. It will be apparent to those skilled in the art that the specific exemplary elements, structures, features, details, configurations, etc., that are disclosed herein can be modified and/or combined in numerous embodiments. All such variations and combinations are contemplated by the inventor as being within the bounds of the conceived invention, not merely those representative designs that were chosen to serve as exemplary illustrations. Thus, the scope of the present invention should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof). To the extent that there is any conflict or discrepancy between this specification as written and the disclosure in any document incorporated by reference herein, this specification as written will control.

What is claimed is:

1. An eye-protection headgear comprising,
an opaque rigid visor comprising a window that consists of an optically-transmissive, clear pane mounted in a through-opening of the opaque rigid visor, with the exclusionary proviso that the window does not comprise an optical filter configured to reduce high intensity visible light;
a flexible fabric bib removably attached to, and extending downward from, a lower edge of the opaque rigid visor;
wherein the opaque rigid visor is pivotably movable between at least a first, shielding position in which a lower edge of the flexible fabric bib is configured to contact the user's chest, and a second, non-shielding position in which a lower edge of at least a forward portion of the flexible fabric bib is configured to be above the level of the eyes of a user of the eye-protection headgear; and,
a head suspension to which the opaque rigid visor is pivotally connected by a pivotal connection that allows the opaque rigid visor to be pivotally moved relative to the head suspension between at least the first, shielding position and the second, non-shielding position.

2. The eye-protection headgear of claim 1 wherein the flexible fabric bib is removably attached to the lower edge of the opaque rigid visor at multiple locations spaced along the extent of the flexible fabric bib and the opaque rigid visor.

3. The eye-protection headgear of claim 2 wherein the attachment of the flexible fabric bib to the lower edge of the opaque rigid visor is by way of attachment studs.

4. The eye-protection headgear of claim 1 wherein when the opaque rigid visor is in the second, non-shielding position, at least the forward portion of the flexible fabric bib is oriented at a positive angle of at least about 30 degrees away from vertical when viewed along a lateral axis of the headgear.

5. The eye-protection headgear of claim 1 wherein at least substantially an entire length of a lower edge of the flexible fabric bib comprises a folded hem that provides a stiffening beam.

6. The eye-protection headgear of claim 1 wherein the headgear comprises a flexible fabric cap extending at least generally rearward from the opaque rigid visor.

7. The eye-protection headgear of claim 6 wherein the flexible fabric bib is provided by a first piece of fabric and wherein the flexible fabric cap is provided by a second piece of fabric that is a separate piece from the first piece of fabric and that is not directly connected to the first piece of fabric.

8. The eye-protection headgear of claim 6 wherein the flexible fabric bib and the flexible fabric cap are first and second, integrally-connected portions of a piece of fabric.

9. The eye-protection headgear of claim 6 wherein when the opaque rigid visor is in the first, shielding position, the flexible fabric cap is configured so that it extends rearward to overlie a crown of a head of the user of the eye-protection headgear.

10. The eye-protection headgear of claim 6 wherein the flexible fabric bib and the flexible fabric cap portion meet each other on first and second lateral sides of the eye-protection headgear so as to collectively provide lateral neck-protection portions of the headgear.

11. The eye-protection headgear of claim 6 wherein the flexible fabric cap comprises at least one opening configured to admit an air-delivery hose of a respiratory-protective apparatus.

12. The eye-protection headgear of claim 6 wherein the flexible fabric cap is removably attached to the opaque rigid visor.

13. The eye-protection headgear of claim 1 wherein the flexible fabric bib is made of flame-retardant fabric.

14. The eye-protection headgear of claim 1 wherein the window is peripherally surrounded by, and defined by, a frame portion of the opaque rigid visor, and wherein the opaque rigid visor is made of a molded opaque thermoplastic polymeric material.

15. The eye-protection headgear of claim 1 wherein the pivotal connection allows the opaque rigid visor to be slidably moved forward and rearward relative to the head suspension.

16. The eye-protection headgear of claim 9 wherein the flexible fabric cap is configured so that when the opaque rigid visor is in the first, shielding position, a portion of the flexible fabric cap is configured so that it resides rearward of an occipital portion of the head of the user.

17. The eye-protection headgear of claim 16 wherein the flexible fabric cap is configured so that when the opaque rigid visor is in the first, shielding position, a portion of the flexible fabric cap is configured so that it resides rearward of a neck of the user.

18. A method of using the eye-protection headgear of claim 1, the method comprising:
fitting the eye-protection headgear on a head of the user of the eye-protection headgear, and
performing at least one operation while wearing the eye-protection headgear.

19. A method of assembling the eye-protection headgear of claim 1, the method comprising:
removably attaching a flexible fabric bib to a lower edge of an opaque rigid visor of a headgear in which the opaque rigid visor comprises a window that consists of an optically-transmissive, clear pane mounted in a through-opening of the opaque rigid visor, with the exclusionary proviso that the window does not comprise an optical filter configured to block high intensity visible light,
so that in the assembled eye-protection headgear, the opaque rigid visor is pivotably movable between at least a first, shielding position in which a lower edge of the flexible fabric bib is configured to contact the user's chest, and a second, non-shielding position in which a lower edge of at least a forward portion of the flexible fabric bib is configured to be above the level of the eyes of a user of the eye-protection headgear.

* * * * *